US00PP18917P2

(12) United States Plant Patent
Korlipara

(10) Patent No.: US PP18,917 P2
(45) Date of Patent: Jun. 10, 2008

(54) ***CORYDALIS* PLANT NAMED 'BERRY EXCITING'**

(50) Latin Name: *Corydalis shimienensis*
Varietal Denomination: Berry Exciting

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 34 days.

(21) Appl. No.: 11/705,664

(22) Filed: Feb. 12, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Annette H Para
(74) *Attorney, Agent, or Firm*—Klarquist Sparkman, LLP

(57) ABSTRACT

A new and distinct form of *Corydalis* plant characterized by its striking soft yellow to lime green foliage, purple flowers, a spreading habit, and excellent vigor.

1 Drawing Sheet

Botanical denomination: *Corydalis shimienensis.*
Variety description: 'Berry Exciting'.

The present invention relates to a new and distinct cultivar of *Corydalis,* of the family *Papaveraceae,* known by the cultivar name, 'Berry Exciting'. This plant originated from a mutation in tissue culture from *Corydalis shimienensis* 'Blackberry Wine', an unpatented plant.

This plant is made unique by the soft yellow to lime green color of its foliage. It has the vigor, spreading habit, and purple flowers of *Corydalis* sp. 'Blackberry Wine'.

The new variety has been reproduced only by asexual propagation (division and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a one-year-old *Corydalis* 'Berry Exciting' grown in a one gallon container in bloom in spring in Canby, Oreg.

DETAILED PLANT DESCRIPTION

The following is a detailed description of the new *Corydalis* cultivar based on observations of less than one-year-old specimens grown in the greenhouse in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart. The color descriptions are all based on The Royal Horticultural Society Colour Chart.

Plant:
- *Form.*—Clumping, herbaceous perennial.
- *Cold hardiness.*—USDA Zone 5.

- *Size.*—Grows to 20 cm tall to top of foliage and 65 cm wide.
- *Vigor.*—Excellent.
- *Roots.*—Fibrous, somewhat succulent, white in color, roots develop easily from divisions.

Stem:
- *Type.*—Decumbent, pentagonal in cross section.
- *Size.*—Grows to 50 cm long and 3 mm wide.
- *Internodes.*—Grow to 11 cm long.
- *Surface texture.*—Glabrous.
- *Color.*—Grey Brown 199A.

Leaf:
- *Type.*—Pinnately decompound, ternate.
- *Arrangement.*—Alternate.
- *Shape.*—Deltoid in outline, each leaflet is ovate to rhomboid.
- *Lobing/Division.*—Each leaflet is irregularly 0 to 3-cleft and the terminal 2-parted and 2-lobed, each lobe entire and mucronate, long petiolate.
- *Venation.*—Palmate.
- *Margins.*—Each lobe is entire on sides.
- *Apex.*—Mucronate.
- *Base.*—Cuneate, oblique.
- *Blade size.*—Grows to 13 cm long and 16 cm wide.
- *Surface texture.*—Glabrous.
- *Petiole description.*—Grows to 10 cm long and 2.5 mm wide, rachis grows to 5.5 cm long, petiolules grow to 3.5 cm long, glabrous, Grey Brown 199A.
- *Leaf color.*—Top side: newest leaves are Yellow Green 144A, young leaves are Yellow Green 144B, and older leaves are Green Yellow 1D with veins and margins Yellow Green 144B. Bottom side: the same, but slightly duller.

Inflorescence:
- *Type.*—Raceme.
- *Number of flowers.*—12 to 14 per raceme.
- *Peduncle description.*—Grows to 15 cm long and 2 mm wide, glabrous, Grey Brown 199A, bracts subtend each pedicel with the bottom two lobed and leaf-like and rest linear.
- *Pedicel description.*—Grow to 9 mm long less than 1 mm wide and are attached to the base of the spur.

*Bloom period.*—May to November in Canby, Oreg. With very hot summers this plant will go summer dormant. Blooms best in cool temperatures of spring and fall.

Flower bud:

*Size.*—2 cm long and 5 mm wide at the widest point prior to opening.

*Description.*—Shaped like a young tadpole, with the nectary spur tip curving down.

*Color.*—Violet 85B on nectary spur and top of tube, White 155A on bottom, lobe area is closest to Purple 79D.

Flower:

*Type.*—Zygomorphic.

*Corolla description.*—Tubular, 2.7 cm long and 11 mm wide at lobe area where it is widest; nectary spur extends back from pedicel for 8 mm and curves slightly down, tube 7 mm long; upper petal 3 mm wide, 2 mm deep, and 6 mm long, hood-like and ridged, entire, ovate, and acute; lower petal is clawed and ridged, claw is 3 mm long and 1.5 mm wide, petal is 3 mm wide, 6 mm long, 3 mm deep, entire, ovate and acute; the two apically fused inner petals are 5 mm long and 2.5 mm wide.

*Color.*—Tube and nectary spur are Purple 79D, inner petals, base of tube, and claw of lower petal are White 155A, the two outer petals are Violet 83A with edges Purple 79A.

*Sepal description.*—2, minute, less than 1 mm deep and wide, reniform, dentate, Violet 85D.

*Pistil description.*—One, linear and 11.5 mm long, ovary 7 mm long and Yellow Green 144A, style 2 mm long and White 155A, stigma is round and flat, 1 mm in diameter, Yellow Green 144A.

*Stamen description.*—2,9 mm long, filaments 6 mm long, flat and translucent, White 155A, anthers 1.5 mm round, pollen Yellow 5D.

*Fragrance.*—Floral.

*Lastingness.*—A raceme blooms for about 3 weeks on the plant.

Fruit and seed: never seen, believed to be sterile.

Diseases and pests:

*Corydalis* are susceptible to aphids, mites, and rust. This new variety has no known immunities.

DESCRIPTION AND COMPARISON OF PARENT PLANT

*Corydalis* 'Berry Exciting' is identical in habit and flower to *Corydalis* 'Blackberry Wine'. The only difference is the foliage color. *Corydalis* 'Blackberry Wine' has grass green leaves and *Corydalis* 'Berry Exciting' has lime green to soft yellow colored leaves.

I claim:

1. A new and distinct form of *Corydalis* plant as hereby illustrated and described.

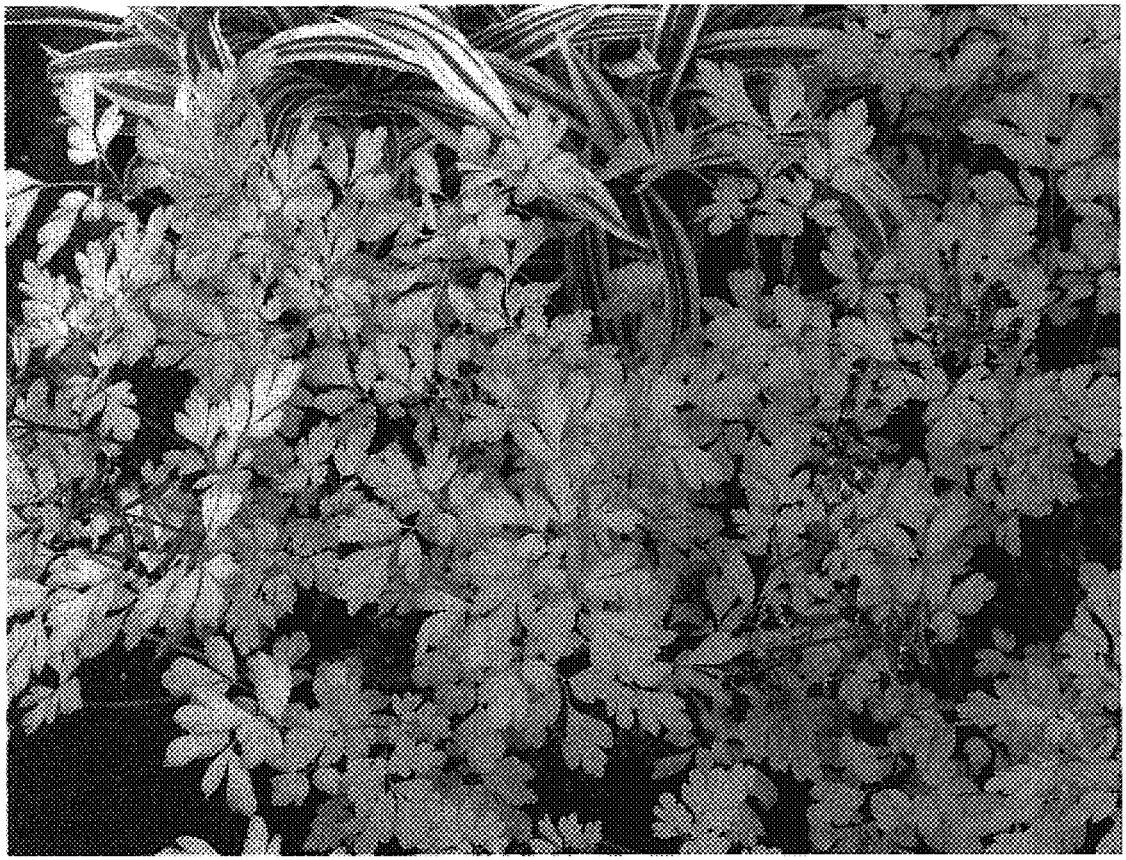

* * * * *